United States Patent [19]

Castillo et al.

[11] Patent Number: 5,985,310
[45] Date of Patent: *Nov. 16, 1999

[54] PRESERVATIVE SYSTEMS FOR PHARMACEUTICAL COMPOSITIONS CONTAINING CYCLODEXTRINS

[75] Inventors: Ernesto J. Castillo, Arlington; Ramon L. Espino, Cleburne, both of Tex.

[73] Assignee: Alcon Laboratories, Inc., Fort Worth, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 09/029,943

[22] PCT Filed: Aug. 8, 1997

[86] PCT No.: PCT/US97/14119

§ 371 Date: Mar. 10, 1998

§ 102(e) Date: Mar. 10, 1998

[87] PCT Pub. No.: WO98/06381

PCT Pub. Date: Feb. 19, 1998

Related U.S. Application Data

[60] Provisional application No. 60/022,453, Aug. 9, 1996.

[51] Int. Cl.$^6$ ............ A61K 47/40; A61K 47/18
[52] U.S. Cl. ............ 424/427; 514/58; 514/740; 514/743; 514/553
[58] Field of Search ............ 424/427; 514/58, 514/743, 740, 553

[56] References Cited

U.S. PATENT DOCUMENTS

| | | | |
|---|---|---|---|
| 4,209,449 | 6/1980 | Mayhew | 260/403 |
| 4,727,064 | 2/1988 | Pitha | 514/58 |
| 4,870,060 | 9/1989 | Muller | 514/58 |
| 5,286,719 | 2/1994 | Fost et al. | 514/114 |
| 5,310,429 | 5/1994 | Chou et al. | 134/6 |
| 5,322,667 | 6/1994 | Sherman | 422/28 |
| 5,376,645 | 12/1994 | Stella et al. | 514/58 |
| 5,411,598 | 5/1995 | Tsai et al. | 134/26 |

FOREIGN PATENT DOCUMENTS

| | | |
|---|---|---|
| 0 076 136 | 9/1982 | European Pat. Off. . |
| 0 119 737 A2 | 9/1984 | European Pat. Off. . |
| 0 149 197 B1 | 7/1985 | European Pat. Off. . |
| 60-149530 | 8/1985 | Japan . |
| 01016718 | 1/1989 | Japan . |
| 6016547 | 1/1994 | Japan . |
| WO 95/30420 | 11/1995 | WIPO . |
| WO 95/30425 | 11/1995 | WIPO . |
| WO 96/14829 | 5/1996 | WIPO . |
| WO 97/10805 | 3/1997 | WIPO . |

OTHER PUBLICATIONS

Kubo et al., "Ophthalmic Solutions of Aspartic Acid Salts Containing Cyclodextrins With No Eye Irritation," *Chemical Abstracts*, vol. 125(16), Abstract No. 204583 (1996).

Loftsson et al., "Interactions Between Preservatives and 2–Hydroxypropyl–β–Cyclodextrin," *Drug Development and Industrial Pharmacy*, vol. 18(13), pp. 1477–1484 (1992).

Malakhova et al., "Cyclodextrins," *Cyclodextrin News*, vol. 8(11), pp. 159–177, (1994).

Miyajima et al., "Interaction of Short–Chain Alkylammonium Salts with Cyclodextrins in Aqueous Solutions," *Chem. Pharm. Bull*, vol. 35(1), pp. 389–393 (1987).

Shinohara et al., "Ophthalmic Solutions Containing Cationic Antiseptics, Cyclodextrins, and EDTA," *Chemical Abstracts*, vol. 125(14), Abstract No. 177471 (1996).

Simpson, "Neutralization of the Antibacterial Action of Quaternary Ammonium Compounds with Cyclodextrins," *FEMS Microbiology Letters*, vol. 90, pp. 197–200 (1992).

Takeuchi et al., "Anti–inflammatory Eyedrops," *Chemical Abstracts*, vol. 125(14), Abstract No. 177444 (1996).

Wakamoto Pharm Co., Ltd, "Storage Stabilised Antiphlogistic Eye Drop Containing Diclofenac Sodium Salt Water Soluble Cyclodextrin Compound," *Derwent Database Week 9408*; AN 94–061985 '08! (1994).

*Primary Examiner*—Gollamudi S. Kishore
*Attorney, Agent, or Firm*—Patrick M. Ryan

[57] ABSTRACT

Disclosed are preservative systems useful in aqueous pharmaceutical compositions containing an active agent and a cyclodextrin. The preservative systems comprise boric acid and one or more compounds selected from the group consisting of $C_{16}$ benzalkonium halide compounds, polymeric quaternary ammonium compounds, and quaternary ammonium alkylene glycol phospholipid derivatives of the following structure

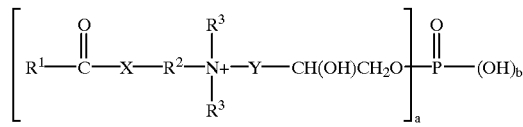

where a+b=3; $R^1$ is $C_8$–$C_{22}$ alkyl or alkene; X is NH, O, or $CH_2$; $R^2$ is $C_2$–$C_6$ alkyl; each $R^3$ is independently $C_1$–$C_{12}$ alkyl or alkene; and Y is nothing or $C_1$–$C_6$ alkyl or alkene; and pharmaceutically acceptable salts thereof.

13 Claims, No Drawings

PRESERVATIVE SYSTEMS FOR PHARMACEUTICAL COMPOSITIONS CONTAINING CYCLODEXTRINS

This application claims priority from U.S. Provisional Application Ser. No. 60/022,453 filed Aug. 9, 1996. This application is also a 371 of PCT/US97/14119 filed Aug. 8, 1997.

BACKGROUND OF THE INVENTION

1. Field of the Invention

The present invention relates generally to the antimicrobial preservation of aqueous pharmaceutical compositions. In particular, the present invention relates to the antimicrobial preservation of pharmaceutical compositions containing cyclodextrins.

2. Description of Related Art

Cyclodextrins are known to possess a number of uses in pharmaceutical formulations. For example, cyclodextrins are known to increase the solubility of insoluble or poorly soluble drug compounds, to increase the stability of chemically labile drugs in pharmaceutical formulations, and to increase the comfort or mask the taste of active drugs. See, U.S. Pat. No. 4,727,064 (Pitha) and EP 0 149 197 B1 (Janssen Pharmaceutica N.V.).

There have been a number of attempts to derivative cyclodextrins in order to decrease toxicity or increase solubility. For example, hydroxy-propyl-beta-cyclodextrin is a derivative which has been shown to have a relatively low toxicity and a high aqueous solubility as compared to the parent compound, beta-cyclodextrin. In addition to hydroxypropyl derivative of beta cyclodextrin, a number of other cyclodextrin derivatives are known. See, for example, U.S. Pat. Nos. 5,376,645 (Stella et al.) and 4,870,060 (Muller).

Typically, multi-dose pharmaceutical products contain preservatives in order to maintain sterility after opening and during use. Antimicrobial preservation of cyclodextrin-containing formulations can present special problems. For example, Loftsson et al., Drug Development and Industrial Pharmacy, 18 (13), 1477–1484 (1992), have investigated interactions between several commonly used preservatives and 2-hydroxypropyl-β-cyclodextrin (HPβCD). Loftsson et al. report that the interactions were twofold: (i) the preservative molecule can displace a drug molecule from the cyclodextrin cavity, thus reducing the solubilizing effects of the cyclodextrin; and (ii) the antimicrobial activity of the preservative can be reduced by the formation of preservative-cyclodextrin inclusion complexes. Specifically, Loftsson et al. report that chlorobutanol, methylparaben and propylparaben have little or no preservative activity in the tested HPβCD solutions. Additionally, Loftsson et al. found that benzalkonium chloride (with the possible exception of the micro-organism, Ps. aeruginosa) and chlorhexidine gluconate did possess significant preservative activity. In contrast, Simpson, FEMS Microbiology Letters, 90, 197–200 (1992), reports that cyclodextrins can inactivate the antimicrobial activity of certain quaternary ammonium compounds. See also, Miyajima et al., Chem. Pharm. Bull., 35(1), 389–393 (1987), regarding the interaction of short-chain alkylammonium salts with cyclodextrins in aqueous solutions, which concluded that α-, β-, and γ-cyclodextrins form complexes with alkylammonium salts having alkyl groups longer than n-butyl, n-hexyl, and n-decyl, respectively.

Benzalkonium chloride (BAC) is the most popular preservative for ophthalmic drug preparations. BAC, as defined in United States Pharmacopeia XIX, is an alkylbenzyldimethyl-ammonium chloride mixture with alkyl chains or homologs beginning with n-$C_8H_{17}$ and extending through higher homologs of $C_{10}$-, $C_{12}$-, $C_{14}$-, and $C_{16}$-alkyl chains. In our attempts to preserve pharmaceutical formulations containing a cyclodextrin with BAC, however, we have found that cyclodextrin-preservative interactions can significantly reduce or inactivate the preservative efficacy of BAC, when BAC is employed at non-toxic levels.

EP 0 119 737 A2 (Takeda Chem. Ind., Ltd.) discloses aqueous pharmaceutical compositions comprising an active ingredient, a cyclodextrin and a phenol derivative as a preservative. The phenol derivative has the formula

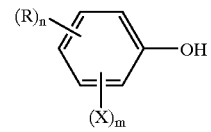

where R is alkyl, X is halogen, n is an integer of 0 to 2, and m is an integer of 1 to 3. According to this reference, formulations containing a cyclodextrin and a paraben preservative (methyl-, ethyl-, propyl-, and butylparaben) suffered a significant decrease in the antimicrobial activity of the preservative, while formulations containing a cyclodextrin and a phenol derivative of the formula above did not.

JP 60149530 A (Takeda Chem. Ind., Ltd.) discloses aqueous compositions of a principal agent and a cyclodextrin where the compositions contain as a preservative a chlorhexidine derivative of the formula

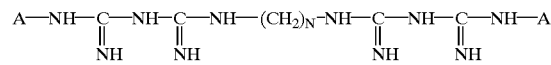

where A is [independently] (un)substituted phenyl; n is 3–9; and the polymethylene chain may be interrupted by an oxygen atom or an aromatic ring.

JP 01016728 A (Santen Seiyaku KK) discloses antiseptic aqueous preparations containing a drug, a cyclodextrin and a cationic surfactant as a preservative. By adding a cyclodextrin or cyclodextrin derivative, cationic surfactants commonly incompatible with certain drugs can be combined. Disclosed cationic surfactants are benzalkonium chloride, benzethonium chloride or chlorohexidine gluconate. Disclosed drugs include sodium hyaluronate, pilocarpine hydrochloride, lysosyme chloride, $Na_2$ chondroitin sulfate, glycyrrhetinate, pirenoxine, sodium chromoglycate, and dimethylisopropylazulene sodium sulfate.

JP 6016547 A (Wakamoto Pharm. Co. Ltd.) discloses eye drop compositions containing diclofenac sodium and a water soluble cyclodextrin compound. The reference also discloses that these compositions can be preserved using benzalkonium chloride, benzethonium chloride and chlorhexidine gluconate as cationic surfactants; methylparaben, ethylparaben, propylparaben and butylparaben as parabens; and phenylethyl alcohol and benzyl alcohol as alcohols.

Even if their antimicrobial preservative efficacy is not significantly reduced by interactions with cyclodextrins, benzyl or phenylethyl alcohol and paraben preservatives may present cytotoxicity, evaporation loss, comfort and/or stability problems. Other compounds or systems capable of effectively preserving pharmaceutical formulations containing cyclodextrins are desirable.

SUMMARY OF THE INVENTION

According to the present invention, aqueous pharmaceutical compositions containing a pharmaceutically active compound and a cyclodextrin can be preserved using a preservative system comprising a combination of boric acid and one or more compounds selected from the group consisting of $C_{16}$ benzalkonium halide compounds, polymeric quaternary ammonium compounds, and quaternary ammonium alkylene glycol phospholipid derivatives.

Thus, the present invention relates to aqueous compositions containing a pharmaceutically active drug compound, a cyclodextrin, and a preservative system selected as described above. The present invention also relates to a method of preserving aqueous pharmaceutical compositions containing a cyclodextrin, wherein the method comprises adding to the composition a preservative system of the type described above.

Among other factors, the present invention is based on the discovery that, unlike BAC, $C_{16}$ benzalkonium halide compounds, polymeric quaternary ammonium compounds and quaternary ammonium alkylene glycol phospholipid derivatives do not interact with cylodextrins in a way that significantly reduces or eliminates their antimicrobial preservative activity.

DETAILED DESCRIPTION OF THE INVENTION

The aqueous compositions of the present invention comprise a pharmaceutically active drug compound, a cyclodextrin, and a preservative system, wherein the preservative system comprises a combination of boric acid and one or more compounds selected from the group consisting of $C_{16}$ benzalkonium halide compounds, polymeric quaternary ammonium compounds, and quaternary ammonium alkylene glycol phospholipid derivatives.

The $C_{16}$ benzalkonium halide compounds useful in the compositions of the present invention have the following structure

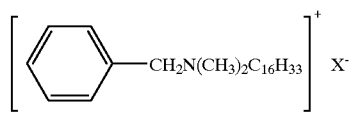

where X=Cl, Br, I, or F. These compounds are known in the art and are either commercially available or can be made using known methods. The most preferred $C_{16}$ benzalkonium halide compound is $C_{16}$ benzalkonium chloride. The $C_{16}$ benzalkonium halide compound is typically used in the compositions of the present invention in an amount from about 0.001 to 1%, preferably from about 0.01 to 0.5%. The most preferred concentration of the $C_{16}$ benzalkonium halide compounds in the compositions of the present invention is about 0.02%. (Unless indicated otherwise, all percentages referred to herein are on a w/w basis).

The polymeric quaternary ammonium compounds useful in the compositions of the present invention are those which have an antimicrobial effect and which are pharmaceutically acceptable. The most preferred polymeric ammonium compounds are those known as polyquaternium-1, otherwise known as Polyquad® or Onamer M®, with a number average molecular weight between 2,000 to 30,000. Preferably, the number average molecular weight of the polyquaternium-1 is between 3,000 to 14,000.

The polymeric quaternary ammonium compounds are generally used in the compositions of the present invention in an amount from about 0.001 to about 3%, preferably from about 0.001 to about 0.1%. The most preferred concentration of polymeric quaternary ammonium compounds is about 0.01%.

The quaternary ammonium alkylene glycol phospholipid derivatives useful in the compositions of the present invention include those having the structure

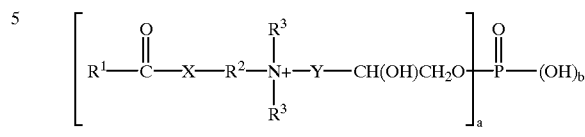

where a+b=3; $R^1$ is $C_8$–$C_{22}$ alkyl or alkene; X is NH, O, or $CH_2$; $R^2$ is $C_2$–$C_6$ alkyl; each $R^3$ is independently $C_1$–$C_{12}$ alkyl or alkene; and Y is nothing or $C_1$–$C_6$ alkyl or alkene. In addition to the acid form of the structure shown above, pharmaceutically acceptable salts of the acid form are also within the scope of present invention. Examples of such salts include the sodium chloride, potassium chloride, and calcium and magnesium salts of the structure shown above. Preferred are the following synthetic phopholipids: cocamidopropyl propylene glycol-dimonium chloride phosphate (sodium chloride salt where $R^1$ is a coconut oil fatty acid alkyl mixture; X is NH; $R^2$ is propyl; $R^3$ is methyl; and Y is $CH_2$); borageamidopropyl phosphatidyl propylene glycol-dimonium chloride (sodium chloride salt where $R^1$ is a boraginaceae oil fatty acid alkyl mixture; X is NH; $R^2$ is propyl; $R^3$ is methyl; and Y is $CH_2$); and cocophosphatidyl propylene glycol-dimonium chloride (sodium chloride salt where $R^1$ is a coconut oil fatty acid alkyl mixture; X is O; $R^2$ is propyl; $R^3$ is methyl; and Y is $CH_2$). The phospholipid compounds described above can be synthesized using known techniques. The three preferred phospholipids are commercially available from, for example, MONA Industries, Patterson, N.J.

The amount of quaternary ammonium alkylene glycol phospholipid derivatives in the compositions of the present invention may range from about 0.01 to about 2%, preferably from about 0.03 to 1.5%. When concentrations approaching the upper limits of these ranges are employed in compositions intended for contact with sensitive tissues, such as topically administrable ophthalmic formulations, the comfort of the compositions may be reduced and additional comfort-enhancing ingredients may be needed (such as emollients typical in the ophthalmic industry: polyethylene glycol, hydroxypropylmethylcellulose, polyvinylalcohol, etc.).

The boric acid used in the compositions of the present invention includes not only boric acid, but also its pharmaceutically acceptable acid addition salts. Accordingly, as used herein, "boric acid" refers to boric acid and its pharmaceutically acceptable acid addition salts. In general, an amount from about 0.3 to about 5% of boric acid is used in the compositions of the present invention. It is preferred to use from about 0.3 to about 3.0%, and it most preferred to use from about 0.5 to about 2.0%.

Suitable cyclodextrins for use in the compositions of the present invention include pharmaceutically acceptable cyclodextrins and cyclodextrin derivatives. Nonionic cyclodextrins are preferred. Most preferred are alkyl derivatives, such as hydroxy-propyl-beta-cyclodextrin. Generally, the concentration of cyclodextrins present in the compositions of the present invention ranges from about 0.5 to about 20%, preferably from about 1 to about 10%.

Any pharmaceutical agent may be included in the compositions of the present invention, particularly both positively-charged and neutral agents (negatively-charged agents may form undesirable complexes with the positively-charged preservative ingredient). For example, pharmaceutical agents which may be incorporated into the compositions of the present invention include, but are not limited to, the racemic and enantiomeric forms and pharmaceutically acceptable salts, amides, esters and prodrugs of the following types of drugs: adrenocorticoids; glucocorticoids; anticoagulants; anticonvulsants; antidepressants; antidiabetics; antihistamines; decongestants; antithyroid agents; antimuscarinics; etc. Preferred are ophthalmic agents including anti-glaucoma agents, such as carbonic anhydrase inhibitors, prostaglandins and prostaglandin derivatives; anti-inflammatory agents, including but not limited to those classified as aryl- or heteroaryl- alkanoic acids, such as diclofenac, bromfenac, flurbiprofen, suprofen, ketorolac, indomethacin and ketoprofen; anti-bacterial and anti-infective agents, such as sulfacetamide sodium, penicillins and cephalosporins; mydriatic and cycloplegic agents, such as phenylephrine, hydroxyamphetamine, tropicamide; and diagnostic agents such as sodium fluorescein. Combinations of pharmaceutical agents may also be used in the compositions of the present invention.

The aqueous compositions of the present invention may additionally include other pharmaceutically acceptable components. For example, comfort enhancing agents, buffers, surfactants, tonicity agents, antioxidants, chelating agents, binding agents, complexing agents, and viscosity modifying agents, including polymers which will undergo a sol-to-gel transition upph exposure to physical or chemical stimuli, such as changes in pH, ion concentration, and/or temperature, may be added to the compositions of the present invention as desired or as necessary.

The compositions of the present invention may be formulated according to techniques known in the art and administered in a variety of ways. For example, the compositions of the present invention may be formulated for parenteral, oral or topical administration. Topically administrable ophthalmic compositions are preferred.

The following examples are presented to illustrate further various aspects of the present invention, but are not intended to limit the scope of the invention in any respect.

EXAMPLE 1

The following formulations were prepared. In Table 1, below, "BAC" means benzalkonium chloride. "$C_{12}$ BAC" means the $C_{12}$ homolog of benzalkonium chloride (dodecyl benzalkonium chloride). "$C_{14}$ BAC" means the $C_{14}$ homolog of benzalkonium chloride (tetradecyl benzalkonium chloride). "$C_{16}$ BAC" means the $C_{16}$ homolog of benzalkonium chloride (hexadecyl benzalkonium chloride). "HPβD" means hydroxy-propyl-beta-cyclodextrin.

TABLE 1

| Ingredient | A | B | C | D | E | F | G | H |
|---|---|---|---|---|---|---|---|---|
| Suprofen | 0.25 | 0.25 | 0.25 | 0.25 | 0.25 | 0.25 | 0.25 | 0.25 |
| Boric Acid | 0.5 | 0.5 | 0.5 | 0.5 | 0.5 | 0.5 | 0.5 | 0.5 |
| NaCl | 0.7 | 0.7 | 0.7 | 0.7 | 0.7 | 0.7 | 0.6 | 0.6 |
| Edetate Disodium | 0.01 | 0.01 | 0.01 | 0.01 | 0.01 | 0.01 | 0.01 | 0.01 |
| NaOH/HCl | q.s. pH = 6.5 | q.s. pH = 6.5 | q.s. pH = 6.5 | q.s. pH = 6.5 | q.s. pH = 6.5 | q.s. pH = 6.5 | q.s. pH = 6.5 | q.s. pH = 6.5 |
| BAC | 0.01 | — | — | — | — | 0.01 | 0.01 | 0.01 |
| $C_{12}$ BAC | — | 0.012 | — | — | — | — | — | — |
| $C_{14}$ BAC | — | — | 0.012 | — | — | — | — | — |
| $C_{16}$ BAC | — | — | — | 0.012 | 0.015 | — | — | — |
| Hamposyl ® L | 0.03 | 0.03 | 0.03 | 0.03 | 0.03 | — | 0.03 | — |
| Monobasic/Dibasic Na Phosphate | — | — | — | — | — | — | 0.1/ 0.03 | 0.1/ 0.03 |
| HPβCD | 2 | 2 | 2 | 2 | 2 | 2 | — | — |
| Glycacil | — | — | — | — | — | — | — | — |
| Polyquaternium-1 | — | — | — | — | — | — | — | — |
| dowicil | — | — | — | — | — | — | — | — |
| cetrimide | — | — | — | — | — | — | — | — |
| lysozyme | — | — | — | — | — | — | — | — |
| phospholipid[1] | — | — | — | — | — | — | — | — |

| Ingredient | I | J | K | L | M | N | O | P | Q | R |
|---|---|---|---|---|---|---|---|---|---|---|
| Suprofen | 0.25 | 0.25 | 0.25 | 0.25 | 0.25 | 0.25 | 0.25 | 0.25 | 0.25 | 0.25 |
| Boric Acid | 0.5 | 0.5 | 0.5 | 0.5 | 0.5 | 0.5 | 0.5 | 0.5 | 1.0 | 0.5 |
| NaCl | 0.8 | 0.7 | 0.7 | 0.7 | 0.7 | 0.7 | 0.7 | 0.7 | 0.3 | 0.7 |
| Edetate Disodium | 0.01 | 0.01 | 0.01 | 0.01 | 0.01 | 0.01 | 0.01 | 0.01 | 0.01 | 0.01 |
| NaOH/HCl | q.s. pH = 6.5 | q.s. pH = 6.5 | q.s. pH = 6.5 | q.s. pH = 6.5 | q.s. pH = 6.5 | q.s. pH = 6.5 | q.s. pH = 6.5 | q.s. pH = 6.5 | q.s. pH = 6.5 | q.s. pH = 6.5 |
| BAC | 0.01 | — | — | — | — | — | — | — | — | — |
| $C_{12}$ BAC | — | — | — | — | — | — | — | — | — | — |
| $C_{14}$ BAC | — | — | — | — | — | — | — | — | — | — |
| $C_{16}$ BAC | — | — | — | — | — | — | — | — | — | 0.015 |
| Hamposyl ® L | — | — | — | — | — | — | — | — | — | — |
| Monobasic\basic Na Phosphate | 0.1/ 0.03 | — | — | — | — | — | — | — | — | — |
| HPβCD | — | 2.0 | 2.0 | 2.0 | 2.0 | 2.0 | 2.0 | 2.0 | 2.0 | 2.0 |
| Glycacil | — | 0.03 | — | — | — | — | — | — | — | — |
| Polyquaternium-1 | — | — | 0.01 | 0.005 | — | — | — | — | — | — |
| dowicil | — | — | — | — | 0.03 | — | — | — | — | — |

TABLE 1-continued

| | | | | | | | | | | |
|---|---|---|---|---|---|---|---|---|---|---|
| cetrimide | — | — | — | — | — | 0.01 | — | — | — | — |
| lysozyme | — | — | — | — | — | — | 0.1 | — | — | — |
| phospholipid[1] | — | — | — | — | — | — | — | 1.5 | — | 0.03 |

[1]cocamidopropyl PG-dimonium chloride phosphate

EXAMPLE 2

In addition to the suprofen formulations appearing in Table 1 above, the betaxolol formulations shown in Table 2, below, were also prepared.

TABLE 2

| | FORMULATION | | |
|---|---|---|---|
| COMPONENTS | AA | AB | AC |
| Betaxolol HCl | 0.56 | 0.56 | 0.56 |
| HPβCD | 7.5 | 7.5 | 7.5 |
| Boric Acid | 0.5 | 0.5 | 0.5 |
| Sodium Chloride | 0.3 | 0.3 | 0.3 |
| EDTA | 0.01 | 0.01 | — |
| BAC | — | 0.015 | — |
| Phospholipid[1] | — | — | 0.03 |
| POLYQUAD | 0.01 | — | — |
| NaOH/HCl QS to pH | 7.0 | 6.6 | 6.58 |
| Purified Water | QS | QS | QS |

[1] = cocamidopropyl PG-dimonium chloride phosphate

EXAMPLE 3

The antimicrobial preservative effectiveness of the compositions of Examples 1 and 2 was determined using an organism challenge test according to the methods described in the United States Pharmacopeia (USP) and European Pharmacopoeia (Ph.Eur.). Samples were inoculated with known levels of gram-positive (*Staphyl-ococcus aureus* ATCC 6538) and gram-negative (*Pseudomonas aeruginosa* ATCC 9027 and *Escherichia coli* ATCC 8739) vegetative bacteria, yeast (*Candida albicans* ATCC 10231) and mold (*Aspergillus niger* ATCC 16404) and sampled at specified intervals to determine if the antimicrobial preservative system was capable of killing or inhibiting the propagation of organisms purposely introduced into the formulation. Despite the fact that the compositions of the present invention are not limited to ophthalmic preparations, USP and/or Ph.Eur. preservative efficacy standards for ophthalmic preparations were used for purposes of comparing the antimicrobial activity of the test compositions. As shown in Table 3, an abbreviated time pull schedule was employed. Based on the data collected, projected pass/fail determinations were made by comparing the log reductions in the respective organism populations to the standards shown in Table 3.

TABLE 3

Abbreviated Schedule of Compendial Preservative Effectiveness Requirements for Ophthalmic Compositions

| | Log Reduction of Organism Population | | |
|---|---|---|---|
| Time Pull | USP | Ph. Eur. A (Target) | Ph. Eur. B (Min) |
| For Bacteria: | | | |
| 6 hours | — | 2 | — |
| 24 hours | — | 3 | 1 |
| 7 days | 3 | — | 3 |
| For Fungi: | | | |
| 7 days | — | 2 | 1 |

— = No requirement at this time pull

The preservative efficacy results for the formulations of Example 1 are shown in Table 4 below, and those for the formulations of Example 2 are shown in Table 5 below.

TABLE 4

Projected Preservative Efficacy Test Results For Formulations of Example 1

| | Log Reduction | | | | | | | Projected Decision | | |
|---|---|---|---|---|---|---|---|---|---|---|
| | 6 Hr | | 24 Hr | | Day 7 | | | | | |
| Formulation | Sa | Pa | Sa | Pa | Sa | Pa | An | USP | PhEurA | PhEurB |
| A | 0.4 | 0.4 | 2.1 | 1.2 | ND | ND | ND | — | F | — |
| B | 0.0 | 0.1 | 0.0 | 0.3 | ND | ND | ND | — | F | F |
| C | 0.0 | 0.1 | 0.0 | 0.8 | ND | ND | ND | — | F | F |
| D | 5.0 | 1.3 | 5.0 | 2.5 | ND | ND | ND | — | F | — |
| E | 5.1 | 2.7 | 5.1 | 3.9 | 5.1 | 5.0 | 4.9 | P | P | P |
| F | 0.0 | 0.3 | 0.2 | 0.6 | ND | ND | ND | — | F | F |
| G | 2.4 | 5.0 | 3.7 | 5.0 | 5.0 | 5.0 | ND | P | P | P |
| G(repeat) | 0.4 | 2.0 | 2.0 | 2.2 | 5.1 | 2.4 | 3.9 | F | F | F |
| H | 2.5 | 5.0 | 4.2 | 5.0 | 5.0 | 5.0 | ND | P | P | P |

TABLE 4-continued

Projected Preservative Efficacy Test Results For Formulations of Example 1

| Formulation | Log Reduction | | | | | | | Projected Decision | | |
|---|---|---|---|---|---|---|---|---|---|---|
| | 6 Hr | | 24 Hr | | Day 7 | | | | | |
| | Sa | Pa | Sa | Pa | Sa | Pa | An | USP | PhEurA | PhEurB |
| H(repeat) | 0.1 | 1.6 | 1.4 | 2.0 | 3.8 | 2.4 | 3.9 | F | F | F |
| I | 5.0 | 3.4 | 5.0 | 5.0 | 5.0 | 5.0 | ND | P | P | P |
| J | 0.2 | 0.3 | 0.3 | 0.4 | ND | ND | ND | — | F | F |
| K | 3.4 | 5.0 | 3.4 | 5.0 | 5.1 | 5.0 | ND | P | P | P |
| K(repeat) | 3.1 | 5.1 | 4.0 | 5.1 | 5.1 | 5.1 | 1.1 | P | F | P |
| K(repeat)* | 2.7 | 5.0 | 3.8 | 5.0 | 5.3 | 5.0 | 1.5 | P | F | P |
| L | 2.6 | 5.1 | 3.7 | 5.1 | 5.1 | 5.1 | 0.8 | P | F | F |
| M | 0.2 | 3.0 | 5.1 | 5.0 | ND | ND | ND | — | F | — |
| N | 0.2 | 2.2 | 0.2 | 3.5 | ND | ND | ND | — | F | F |
| O | 0.1 | 0.5 | 0.1 | 1.2 | ND | ND | ND | — | F | F |
| P | 5.1 | 5.0 | 5.1 | 5.0 | 5.1 | 5.0 | ND | P | P | P |
| Q | 3.1 | 5.0 | 5.3 | 5.0 | 5.3 | 5.0 | 1.6 | P | F | P |
| Q(repeat)** | 4.8 | 3.6 | 5.1 | 5.1 | 5.1 | 5.1 | 1.0 | P | F | P |
| R | 5.3 | 2.1 | 5.3 | 3.3 | 5.3 | 4.1 | 5.1 | P | P | P |

\* Boric acid = 1.0%, NaCl = 0.3%
\*\*Boric acid = 0.3%, NaCl = 0.7%
ND = not measured

TABLE 5

Projected Preservative Efficacy
Test Results For Formulations of Example 2

| Formulation | Log Reduction | | | | | | | Projected Decision | | |
|---|---|---|---|---|---|---|---|---|---|---|
| | 6 Hr | | 24 Hr | | Day 7 | | | | | |
| | Sa | Pa | Sa | Pa | Sa | Pa | An | USP | PhEurA | PhEurB |
| AA | 5.3 | 5.1 | 5.3 | 5.1 | 5.3 | 5.1 | 1.8 | P | F | P |
| AB | 0.0 | 2.8 | 0.1 | 4.1 | 1.0 | 5.1 | 2.7 | F | F | F |
| AC | 0.0 | 1.8 | 1.1 | 4.6 | 2.4 | 5.1 | 2.1 | F | F | F |

As illustrated in Table 4, formulations containing HPβCD and a preservative system comprising boric acid and a preservative compound selected from the group consisting of $C_{16}$ benzalkonium halide compounds, polymeric quaternary ammonium compounds, and alkylaminopropylene glycol phospholipid compounds (Formulations D, E, K, L, P, Q, and R) possess superior preservative efficacy compared to those formulations containing HPβCD, boric acid, and other preservatives, such as BAC, $C_{12}$- or $C_{14}$-benzalkonium chloride, etc. (Formulations A, B, C, F, J, M, N, & O). Formulations G, H & I (all of which contained boric acid and BAC), also performed well in the preservative efficacy assay, but none of these formulations contained HPβCD.

As shown in Table 5, Formulation AA (preservative system=polyquaternium-1 and boric acid) possesses superior preservative efficacy compared to formulation AB (preservative system=boric acid and BAC). Formulation AC (preservative system=boric acid and cocamidopropyl PG-dimonium chloride phosphate) did not meet the preservative efficacy standards, although Formulations P & Q in Table 4 (containing a different active but the same preservative system) were able to meet the efficacy standards.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. In a preserved aqueous pharmaceutical composition comprising a therapeutically effective amount of a pharmaceutically active agent, a chelating agent, a cyclodextrin and an antimicrobial preservative, the improvement wherein the preservative comprises a combination of boric acid and an antimicrobial preservative compound consisting essentially of a compound selected from the group consisting of $C_{16}$ benzalkanium halide compounds in an amount from about 0.01–0.5% by weight and polymeric quaternary ammonium compounds in an amount from about 0.001–3% by weight.

2. The composition of claim 1 wherein the preservative compound is a $C_{16}$ benzalkonium halide and the halide is selected from the group consisting of chloride, bromide, iodide, and fluoride.

3. The composition of claim 1 wherein the preservative compound is a polymeric quaternary ammonium compound.

4. The composition of claim 3 wherein the polymeric quaternary ammonium compound is polyquaternium-1.

5. The composition of claim 4 wherein the concentration of the preservative compound is from about 0.001 to about 0.1% (w/w).

6. The composition of claim 1 wherein the concentration of boric acid is from about 0.3 to about 5 percent by weight.

7. The composition of claim 1 wherein the concentration of cyclodextrin is from about 0.5 to about 20% (w/w).

8. The composition of claim 7 wherein the cyclodextrin is hydroxy-propyl-beta-cyclodextrin.

9. A method of antimicrobial preservation of an aqueous pharmaceutical composition comprising a therapeutically effective amount of a pharmaceutically active agent, a chelating agent and a cyclodextrin wherein the method comprises adding to the composition a combination of boric acid and an antimicrobial preservative compound consisting essentially of a compound selected from the group consisting of $C_{16}$ benzalkonium halide compounds in an amount from about 0.01–0.5% by weight and polymeric quaternary ammonium compounds in an amount from about 0.001–3% by weight.

10. The method of claim 9 wherein the preservative compound is a $C_{16}$ benzalkonium halide and the halide is selected from the group consisting of chloride, bromide, iodide, and fluoride.

11. The method of claim 9 wherein the preservative compound is a polymeric quaternary ammonium compound.

12. The method of claim 11 wherein the polymeric quaternary ammonium compound is polyquaternium-1.

13. The method of claim 9 wherein the concentration of cyclodextrin is from about 0.5 to about 20% (w/w).

* * * * *